US008314267B2

(12) United States Patent
Brandvold

(10) Patent No.: US 8,314,267 B2
(45) Date of Patent: Nov. 20, 2012

(54) CARBOHYDRATE ROUTE TO PARA-XYLENE AND TEREPHTHALIC ACID

(75) Inventor: Timothy A. Brandvold, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 623 days.

(21) Appl. No.: 12/492,182

(22) Filed: Jun. 26, 2009

(65) Prior Publication Data

US 2010/0331568 A1 Dec. 30, 2010

(51) Int. Cl.
*C07C 51/255* (2006.01)
(52) U.S. Cl. ...................................................... 562/412
(58) Field of Classification Search ......................... None
See application file for complete search history.

(56) References Cited

U.S. PATENT DOCUMENTS

| 3,864,277 | A | * | 2/1975 | Kovach | 502/425 |
| 4,590,283 | A | | 5/1986 | Gaset et al. | 549/488 |
| 4,740,605 | A | | 4/1988 | Rapp | 549/483 |
| 5,250,487 | A | * | 10/1993 | Wirtz et al. | 502/243 |
| 5,430,172 | A | * | 7/1995 | Grammenos et al. | 560/35 |
| 6,281,162 | B1 | | 8/2001 | Smith et al. | 502/344 |
| 6,492,571 | B1 | * | 12/2002 | He et al. | 585/710 |
| 6,706,900 | B2 | | 3/2004 | Grushin et al. | 549/489 |
| 7,432,382 | B2 | | 10/2008 | Sanborn et al. | 549/502 |
| 2003/0148257 | A1 | * | 8/2003 | Berkowitz et al. | 435/4 |

FOREIGN PATENT DOCUMENTS

| GB | 876463 | 9/1961 |
| WO | 2007075370 | 7/2007 |
| WO | 2008019219 | 2/2008 |
| WO | 2008151178 | 12/2008 |

OTHER PUBLICATIONS de la Hoz et al. (Synlett, 2001, 6, 753).*
Evans et al, "Formation of aromatic hydrocarbons due to partial oxidation reactions in biomass gasification," *National Renewable Energy Laboratory*, Golden Co 80401 http://www.anl.gov/PCS/acsfuel/preprint%20archive/Files/44_2_ANAHEIM_03-99_0256.pdf.
vanDam et al., "The conversion of fructose and glucose in acidic media: formation of hydroxymethylfurfural," *Delft University of Technology, Laboratory of Organic Chemistry, GA Delft (the Netherlands) Industrial Chemistry* vol. 38, Issue 3, p. 95-101; published online Oct. 23, 2006.
Asghari et al., "Acid-catalyzed production of 5-hydroxymethylfurfural from D-fructose in subcritical water," *Industrial and Engineering Chemistry Research* 45(7) 2006 p. 2163-2173 American Chemical Society.
Barrett et al., "Single-reactor process for sequential aldol-condensation and hydrogenation of biomass-derived compounds in water," *Applied Catalysis B: Environmental* v 66, n 1-2, Jun. 20, 2006, p. 111-118.
Román-Leshkov et al., "Production of dimethylfuran for liquid fuels from biomass-derived carbohydrates," *Nature* 447, p. 982-985; Jun. 21, 2007.
Petkewich, *Chemical and Engineering News* 85(26) 2007 p. 8 American Chemical Society.
Zhao et al. "Metal chlorides in ionic liquid solvents conver sugars to 5-hydroxymethylfurfural," *Science* Jun. 15, 2007: vol. 316. No. 5831, p. 1597-1600.
Blommel et al., "Production of conventional liquid fuels from sugars," *Virent Technology* (white paper), http://www.virent.com/BioForming/Virent_Technology_Whitepaper.pdf, 2008.
Lange et al., "Lignocellulose conversion: an introduction to chemistry, process and economics," *Shell Global Soluions*, The Netherlands; shortened version from *Catalysis for Renewables* (Centi and van Santen, eds.) Wiley-VCH, Weinheim 2007, Biofuels, Bioproducts and Biorefining,vol. 1, issue 1, p. 39-48; published online: Jul. 18, 2007.

* cited by examiner

*Primary Examiner* — Johann Richter
*Assistant Examiner* — Jennifer C Sawyer
(74) *Attorney, Agent, or Firm* — David J Piasecki

(57) ABSTRACT

Catalytic processes for the conversion of 2,5-dimethyl furan (DMF) to para-xylene are described. Para-xylene is a key product that is currently obtained commercially from petroleum sources. However, it has now been determined that the cycloaddition of ethylene to DMF provides an alternative route to para-xylene. Advantageously, the DMF starting material for the processes may be synthesized from carbohydrates (e.g., glucose or fructose), thereby providing a pathway that relies at least partly, if not completely, on renewable feedstocks.

18 Claims, 1 Drawing Sheet

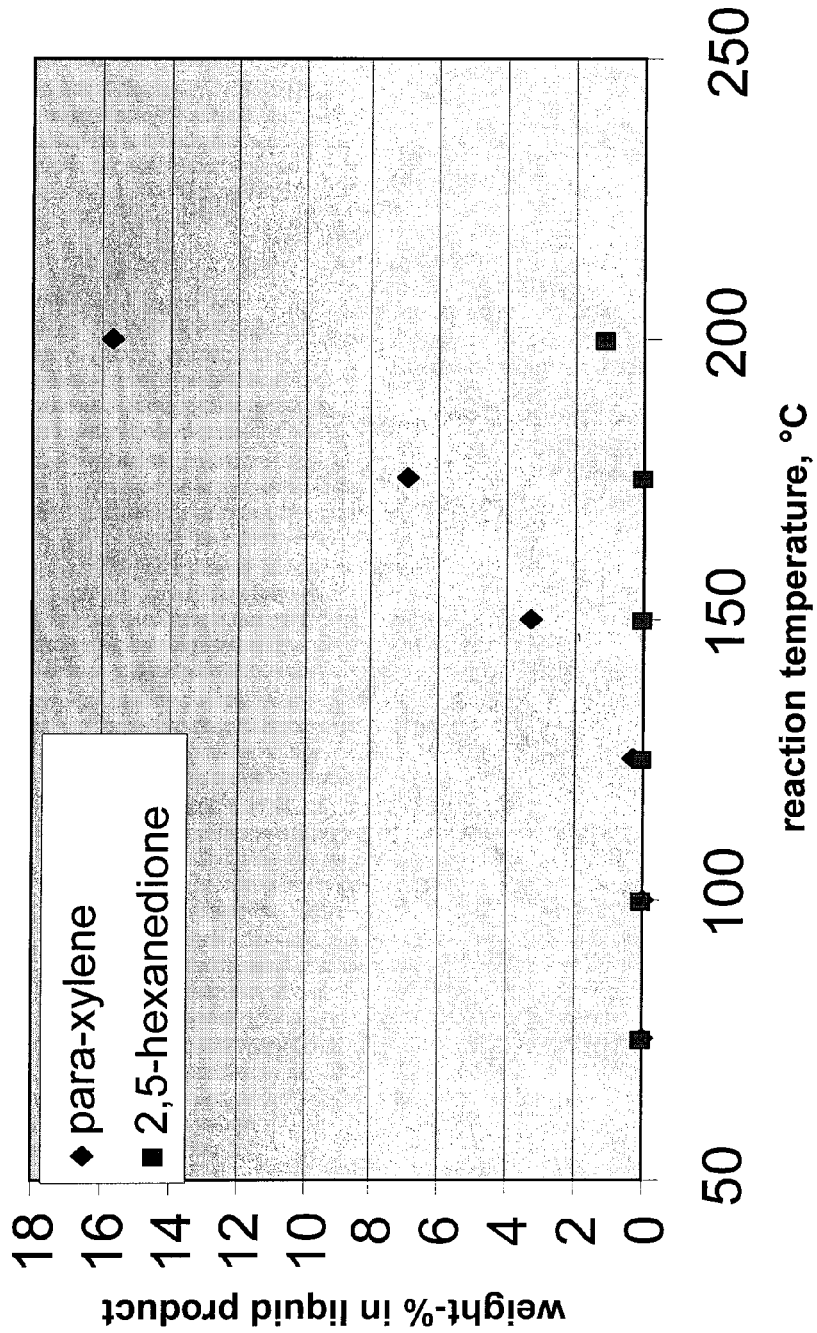

CARBOHYDRATE ROUTE TO PARA-XYLENE AND TEREPHTHALIC ACID

FIELD OF THE INVENTION

The present invention relates to the production of para-xylene from 2,5-dimethylfuran (DMF) and ethylene. The invention relates more particularly to overall bio-based pathways for making para-xylene and its oxidation product, terephthalic acid, from carbohydrates such as hexoses (e.g., glucose or fructose).

DESCRIPTION OF RELATED ART $C_8$ alkylaromatic hydrocarbons are generally considered to be valuable products, with a high demand for para-xylene. In particular, the oxidation of para-xylene is used to commercially synthesize terephthalic acid, a raw material in the manufacture of polyester fabrics. Major sources of para-xylene include mixed xylene streams that result from the refining of crude oil. Examples of such streams are those resulting from commercial xylene isomerization processes or from the separation of $C_8$ alkylaromatic hydrocarbon fractions derived from a catalytic reformate by liquid-liquid extraction and fractional distillation. The para-xylene may be separated from a para-xylene-containing feed stream, usually containing a mixture of all three xylene isomers, by crystallization and/or adsorptive separation. The latter technique has captured the great majority of the market share of newly constructed plants for the production of para-xylene.

Growing concerns related to the production of hydrocarbon fuel components and petrochemicals such as para-xylene are the high costs and potential environmental consequences, such as greenhouse gas emissions, associated with the conventional use of petroleum-based feedstocks. An increasingly important objective of the chemical and petrochemical industries is therefore the identification of feedstocks based on renewable rather than depleting resources. However, the difficulty in converting natural 6-carbon carbohydrate building blocks such as glucose or fructose to desirable end products has hindered progress in some important areas. Recent studies have shown the feasibility of converting hexose carbohydrates to 2,5-dimethylfuran (DMF). For example, Leshkov, Y. R. et al. report the production of 5-hydroxymethylfurfural (HMF) in high yields by the acid-catalyzed dehydration of fructose, followed by the selective hydrogenation of HMF to DMF using a copper-based catalyst (NATURE, June 2007, (447):982-5). Also, Zhao, H. et al. describe the effective synthesis of HMF, starting with glucose, in the presence of a metal halide (e.g., chromium (II) chloride) in 1-alkyl-3-methylimidazolium chloride (SCIENCE, June 2007, (316):1597-1600). Also, U.S. Pat. No. 7,385,081 describes the synthesis of terephthalic acid from carbohydrate derivatives.

Renewable biomass resources are therefore useful in the synthesis of transportation fuel components, including DMF, having favorable research octane numbers and other characteristics that render them suitable substitutes for petroleum-derived products. There is an ongoing need for processes to synthesize, from bio-based feedstocks, additional compounds that are traditionally products of the petroleum and/or petrochemical industries.

SUMMARY OF THE INVENTION

The present invention is associated with the discovery of catalytic processes for the conversion of 2,5-dimethyl furan (DMF) to para-xylene, which is currently a key chemical product from commercial oil refineries. More particularly, it has now been determined that the cycloaddition of ethylene to DMF under certain conditions, followed by additional transformations, can be used to produce para-xylene in high yields. Advantageously, the DMF starting material for the processes may be synthesized from carbohydrates, thereby providing a production route to para-xylene that relies at least partly on renewable feedstocks. For example, the use of glucose or fructose as a source of DMF results in a process in which 6 of the 8 (75%) para-xylene carbon atoms originates from a carbohydrate. Moreover, if the ethylene used as a reactant in processes according to the invention is obtained from biomass ethanol, then the para-xylene produced is completely derived (i.e., all 8 of its 8 carbon atoms) from annually renewable feedstock.

Embodiments of the invention are directed to para-xylene production processes comprising reacting DMF with ethylene under cycloaddition reaction conditions and in the presence of a catalyst to produce para-xylene. Representative cycloaddition reaction conditions include a temperature from about 100° C. (212° F.) to about 300° C. (572° F.), an ethylene partial pressure from about 10 (150 psig) to about 100 barg (1500 psig), and a reactor residence time from about 1 hour to about 48 hours. The processes may be performed batchwise or in a continuous manner, for example by passing the DMF and ethylene reactants continuously over a fixed bed of catalyst. A representative catalyst is activated carbon (e.g., in a solid, powder form), and particularly carbon that has been activated by washing with an acid such as $H_3PO_4$. Other solid materials, and particularly those having a high surface area (e.g., zeolitic or non-zeolitic molecular sieves) and/or adsorptive capacity for the aromatic and olefinic feed components, may also be used as catalysts. Any of these catalysts may optionally be promoted with an alkali or alkaline earth metal promoter.

Advantageously, it has been found that the cycloaddition reaction conditions and catalyst can provide at least about 50% conversion of the DMF, with para-xylene representing at least about 60%, on a molar basis, of the converted DMF (i.e., at least about 60% selectivity to para-xylene, or at least about 0.6 moles of para-xylene produced for each mole of DMF converted). That is, the selectivity to para-xylene is such that this compound is produced in an amount representing at least about 30% of the theoretical yield (i.e., based on 100% DMF conversion and 100% selectivity).

Therefore, according to embodiments of the invention, the conversion of a hexose such as glucose or fructose to 5-hydroxymethylfurfural (HMF) followed by selective hydrogenation of HMF to DMF provides a basis for para-xylene production using at least one annually renewable carbohydrate feedstock. Oxidation of the para-xylene with oxygen, according to conventional methods, provides a similarly "green" pathway to terephthalic acid, which is valuable intermediate in the manufacture of polymers that to date have relied commercially on petroleum-based feedstocks. Additional embodiments of the invention are therefore directed to carbohydrate based processes for producing para-xylene or terephthalic acid comprising converting a hexose such as glucose or fructose to HMF and then to DMF, and reacting the DMF as described above to produce para-xylene, which may optionally be oxidized to terephthalic acid.

These and other embodiments and aspects of the invention are apparent from the following Detailed Description.

BRIEF DESCRIPTION OF THE DRAWING

FIG. 1 shows the amounts of para-xylene and byproduct 2,5-hexanedione obtained after 4 hours in a reaction liquid, initially all 2,5-dimethylfuran, as a function of temperature. In the batch autoclave experiments, the liquid was with pressurized to 35 barg (500 psig) with ethylene in the presence of an activated carbon catalyst.

DETAILED DESCRIPTION

As discussed above, the present invention is associated with processes for the production of para-xylene from 2,5-dimethylfuran (DMF) that may be derived from carbohydrates. Aspects of the invention are particularly associated with the discovery of suitable catalysts and reaction conditions for effectively carrying out this synthesis. Without being bound by theory, the reaction is believed to proceed through the Diels-Alder cycloaddition of ethylene to the furan ring of DMF, followed by ring opening of the oxabicycloheptene derivative with the elimination of water (dehydration) to generate para-xylene. It has now been determined that suitable catalysts and reaction conditions can greatly improve para-xylene productivity or yield, especially compared to thermal or non-catalytic reactions. The terms "catalyst" and "catalytic" are meant to encompass agents that reduce the activation energy needed for a desired reaction, as well as promoters that enhance the effectiveness of such agents.

Suitable catalysts include carbon and particularly activated carbon having a high surface area, for example of at least about 700 square meters per gram ($m^2$/gram), as measured according to the BET method (ASTM 6556-09). Generally, the surface area is in the range from about 700 to about 3000 $m^2$/gram and often from about 700 to about 1500 $m^2$/gram. Catalysts of particular interest include carbon that is activated by washing with an acid, for example, phosphoric acid, to provide the high surface area in these representative ranges and a possibly a number of other desirable properties. Such properties include a total oxygen content of at least about 1% by weight (e.g., in the range from about 1% to about 20%, and often from about 1% to about 10%, by weight).

Thermal processing or activation can also be used to obtain porous carbon particles having a large internal surface area. Regardless of whether the activation is performed chemically or thermally, the activated carbon particles may be granular, spherical, pelletized, or powdered, as supplied by a number of commercial manufacturers, including Norit Americas, Inc. (Marshall, Tex. USA), Japan EnviroChemicals (Tokyo, Japan), Jacobi Carbons AB (Kalmar, Sweden), and Calgon Carbon Corporation (Pittsburgh, Pa.). A representative average particle size of a powdered activated carbon that is used in the methods described herein is less than about 300 microns (50 mesh) and often in the range from about 50 microns (300 mesh) to about 300 microns (50 mesh). Screening may be used in some cases to achieve a desired average particle size.

In general, the activated carbon is derived from an organic source, such as wood, ground coconut shells, etc. Various forms of activated carbon include a surface oxidized activated carbon, a graphite, a graphite oxide, or a carbon nanomaterial. Carbon nanomaterials include, but are not limited to, carbon nanotubes, carbon nanohorns, carbon nanofibers, buckyballs, etc. Activated carbon materials also include those having one or more surface modifications, for example, performed by covalently bonding of acidic or basic materials to control acidity and/or by the incorporation of one or more metals that is catalytically active for the conversion of adsorbed organic compounds. Such surface modifications can therefore supplement (promote) the catalytic activity of the activated carbon for the desired conversion of DMF and ethylene to para-xylene.

In addition to activated carbon, a number of other materials having a relatively high BET surface area (e.g., at least about 200 $m^2$/gram, and often in the range from about 200 $m^2$/gram to about 500 $m^2$/gram), as well as having sufficient capacity for the adsorption of organic reactants, may be used as solid catalysts. These materials include inorganic oxides such as silica (e.g., in the form of a silica gel), alumina, zirconia, etc., as well as zeolitic molecular sieves and non-zeolitic molecular sieves. Zeolitic molecular sieves suitable for use as catalysts are crystalline aluminosilicates which in the calcined form may be represented by the general formula:

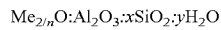

$$Me_{2/n}O:Al_2O_3:xSiO_2:yH_2O$$

where Me is a cation, n is the valence of the cation, x has a value of from about 5 to 100, and y has a value of from about 2 to 10. Zeolites are described in detail by D. W. Breck, *Zeolite Molecular Sieves*, John Wiley and Sons, New York (1974), and elsewhere.

Non-zeolitic molecular sieves include molecular sieves that are of the chemical composition, on an anhydrous basis, expressed by the empirical formula: $(EL_xAl_yP_z)O_2$ where EL is an element selected from the group consisting of silicon, magnesium, zinc, iron, cobalt, nickel, manganese, chromium and mixtures thereof, x is the mole fraction of EL and is at least 0.005, y is the mole fraction of Al and is at least 0.01, z is the mole fraction of P and is at least 0.01, and x+y+z=1. When EL is a mixture of metals, x represents the total amount of the element mixture present. Preferred elements (EL) are silicon, magnesium and cobalt, with silicon being especially preferred. These non-zeolitic molecular sieves are also referred to as "ELAPOs". The preparation of various ELAPOs are known in the art and described, for example, in U.S. Pat. No. 7,317,133, U.S. Pat. No. 5,191,141, U.S. Pat. No. 4,554,143, U.S. Pat. No. 4,440,871, U.S. Pat. No. 4,853,197, U.S. Pat. No. 4,793,984, U.S. Pat. No. 4,752,651, and U.S. Pat. No. 4,310,440.

As indicated above, any of the above solid catalysts may incorporate a metal promoter having catalytic activity for the desired conversion of DMF to para-xylene. Representative metals include alkali and alkaline earth metals, as well as rare earth and transition metals. Combinations of two or more metals may be used in conjunction with any of the solid catalysts described above (e.g., as support materials).

The reaction of DMF with ethylene proceeds in the presence of a catalyst as discussed above under suitable cycloaddition reaction conditions. Advantageously, the use of solvents (e.g., dimethylsulfoxide) that do not participate the desired reaction pathway can be minimized or even eliminated. According to some embodiments, therefore, the cycloaddition reaction conditions include a reaction mixture that is solvent-free or substantially solvent-free (i.e., contains less than about 10%, less than about 5%, or even less than about 1% of a solvent). Exemplary temperatures in the reactor or reaction zone in which the catalyst is disposed (e.g., in a batch reactor or as a fixed or moving bed in a continuous reaction system) are in the range from about 100° C. (212° F.) to about 300° C. (572° F.), and often from about 150° C. (302° F.) to about 225° C. (437° F.). Favorable cycloalkylation reaction conditions also include an ethylene partial pressure of at least about 10 barg (145 psig), generally in the range from about 10 barg (145 psig) to about 100 barg (1450 psig), and often in the range from about 20 barg (290 psig) to about 50 barg (725 psig). The total pressure is typically from about 2% to about 50% higher than the ethylene partial pressure, due to the contributions, to the overall pressure in the reactor or reaction zone, of (i) the vapor pressure of DMF at the reaction temperature, and/or (ii) possible diluents and/or impurities (e.g., ethane).

Whether the reaction is carried out batchwise or continuously, the cycloaddition reaction conditions also generally include a reactor residence time in the range from about 1 hour to about 48 hours, and normally from about 3 hours to about 30 hours. The reactor residence time, however, may be significantly reduced in the case of a continuous process in which unconverted DMF and/or ethylene are recycled to provide a relatively high overall conversion, even if the per-pass conversion is significantly less. Reactant DMF may be continuously fed to a cycloaddition reaction zone, for example, at a liquid hourly space velocity (LHSV) from about 0.05 $hr^{-1}$ to about 5 $hr^{-1}$. As is understood in the art, the Liquid Hourly Space Velocity (LHSV, expressed in units of $hr^{-1}$) is the volumetric liquid flow rate over the catalyst bed divided by the bed volume and represents the equivalent number of catalyst bed volumes of liquid processed per hour. The LHSV is therefore closely related to the inverse of the reactor residence time.

In an exemplary continuous process, the reactants DMF and ethylene are continuously fed to one or more reactors containing a fixed bed of the catalyst (e.g., in a swing-bed reactor system having multiple fixed bed reactors), and a product comprising the converted para-xylene is continuously withdrawn together with unconverted reactants and reaction byproducts such as 2,5-hexanedione. The unconverted materials are preferably separated, for example, based on differences in their relative volatility using one or more separation operations (e.g., flash separation or distillation) employing a single stage or multiple stages of vapor-liquid equilibrium contacting. In some cases, it may be desirable to convert 2,5-hexanedione, which is a hydration byproduct of DMF, back to DMF to improve product yields. The conversion of 2,5-hexanedione to DMF is described, for example, by Bautista et al., CATALYSIS LETTERS, 1999, 60(3): 145-9.

According to a specific embodiment, unconverted ethylene, together with low-boiling byproducts and impurities, is separated from the cycloaddition reaction zone effluent using a single-stage flash separation. The liquid bottoms product of this flash separation is then passed to at least one multi-stage distillation column to separately recover purified para-xylene and unconverted DMF. The unconverted DMF and/or unconverted ethylene may be recycled to the cycloaddition reaction zone, optionally after purging a portion of either or both of these streams to limit the accumulation of byproducts having similar boiling points. According to a particular continuous operation, the flow rate of ethylene reactant to the cycloaddition reactor or reaction zone is controlled to maintain a desired total pressure. Such an operation based on pressure demand ensures that ethylene is fed at a rate that matches essentially its consumption plus losses due to dissolution and possibly a gas purge (vent). In a particular embodiment without a purge of excess ethylene (i.e., without an amount of ethylene in excess of that used in converting DMF), the ethylene recovered from downstream separation of the cycloaddition reactor effluent (e.g., in a flash separator) is essentially the amount dissolved in the liquid DMF and para-xylene at the pressure and temperature of the cycloaddition reaction zone. Process economics in this case, or even in cases in which an ethylene purge is used, may favor the use of once-through rather than recycle ethylene.

Whether a batch or a continuous process is used for the catalytic conversion of DMF to para-xylene, the cycloaddition reaction conditions generally provide a DMF conversion (which may be a per-pass conversion in the cycloaddition reaction zone, in the case of operation with the recycle of unconverted DMF) of at least about 50%, for example from about 50% to about 90% and often from about 50% to about 75%. The recycle of unconverted DMF, for example to extinction or nearly extinction, can provide an overall conversion that is complete or nearly complete. Of the converted DMF, the selectivity to para-xylene is generally at least about 60%, meaning that at least about 0.6 moles of para-xylene are produced for each mole of DMF converted. Typical selectivities to para-xylene are from about 60% to about 85%. In view of these representative conversion and selectivity values, the overall yield of para-xylene is generally at least about 30%, typically from about 30% to about 80%, and often from about 30% to about 65%, of the theoretical yield based on complete conversion of DMF with a stoichiometric amount (1:1 molar) of ethylene to para-xylene and no byproduct formation.

Aspects of the present invention are therefore directed to methods for producing para-xylene, which include the catalytic cycloaddition of ethylene to DMF and thereby advantageously allow for the use of a carbohydrate and particularly a hexose (e.g., glucose or fructose) as a starting material. In particular, the DMF may be obtained from the conversion of the hexose to HMF, followed by the hydrogenation of HMF to DMF. At least 6 of the carbon atoms of the para-xylene (i.e., those originating from the hexose) may therefore be derived from a renewable feedstock. Moreover, the use of biomass-derived ethanol as a source of feed ethylene can render the entire para-xylene molecule as originating from "green" sources. Particular processes for producing para-xylene, as described herein, therefore include converting a hexose such as glucose or fructose to HMF, hydrogenating the HMF to DMF, and reacting the DMF with ethylene under cycloaddition reaction conditions and in the presence of a catalyst to produce the para-xylene. Further processes according to invention include these features as well as the additional element of oxidizing the para-xylene with oxygen to produce terephthalic acid, a precursor of valuable materials that are, to date, produced commercially only from petroleum-based sources. Those having skill in the art, with the knowledge gained from the present disclosure, will recognize that various changes can be made in these methods without departing from the scope of the present disclosure. The subject matter described herein is therefore representative of the present invention and its associated advantages and is not to be construed as limiting the scope of the invention as set forth in the appended claims.

The following examples are set forth as representative of the present invention. These examples are not to be construed as limiting the scope of the invention as these and other equivalent embodiments will be apparent in view of the present disclosure and appended claims.

COMPARATIVE EXAMPLE 1

Non-Catalytic Conversion of DMF to Para-Xylene

An 11 gram sample of 2,5-dimethylfuran (DMF) was charged to an autoclave having a volume of 75 $cm^3$ that was fitted with a gas inlet, thermocouple, pressure transducer, and magnetic stir bar. The autoclave was sealed, pressurized at room temperature with ethylene, and heated to a reaction temperature of 150° C. (302° F.). After a 24-hour reaction period with an initial pressure in the autoclave of 500 psig (35 barg), the reaction liquid was analyzed.

In the absence of an added catalyst, the reaction liquid was primarily unconverted DMF and contained only about 3-4% by weight of para-xylene.

EXAMPLE 1

Catalyst Screening Studies

The experimental procedure described in Comparative Example 1 was repeated in several additional autoclave tests, but in each case with the addition of a solid catalyst in a particle form (granular or powdered) at addition amounts of about 2% by weight, relative to DMF. Also, some of these screening tests were performed at 175° C. (347° F.) in addition to 150° C. (302° F.). The catalysts tested were $ZnCl_2$, rare-earth exchanged Y zeolite (RE-Y), activated carbon, silica gel, and γ-alumina. By introducing a solid catalyst into the autoclave, the amount of para-xylene in the reaction liquid at the end of the 24-hour reaction period was substantially increased, relative to Comparative Example 1, for all catalysts tested. For tests using 2% by weight of activated carbon, the para-xylene amount exceeded 40% by weight.

EXAMPLE 2

Catalytic Activity of Activated Carbon Samples

A number of commercial activated carbon samples from Norit Americas, Inc. (Marshall, Tex. USA), Japan Enviro-Chemicals (Tokyo, Japan), Jacobi Carbons AB (Kalmar, Sweden), and Calgon Carbon Corporation (Pittsburgh, Pa.) were tested using the experimental procedures according to Example 1. Granular carbons were sized to less than 100 mesh (0.15 mm). The samples had BET surface areas ranging from 700-1300 $m^2$/gram and total pore volumes (measured by nitrogen adsorption) ranging from 0.45-1.2 $cm^3$/gram. The use of acid washing for activation of the carbon resulted in a total oxygen content ranging from 1% to as high as 18% by weight for the activated carbon samples that were tested.

For the best-performing activated carbon samples, the liquid product after the reaction period contained 40-55% by weight of para-xylene, and the para-xylene accounted for 65-78% of the total weight of all converted materials, indicating good selectivity for this product. One of the byproducts identified in the liquid product analysis was 2,5-hexanedione (HDO).

EXAMPLE 3

Effect of Reaction Temperature

One of the activated carbon samples used as a catalyst in Example 2 was tested in a number of autoclave experiments as described in Example 1, but with varying reactor temperatures and a total reaction time of only 4 hours. The composition of the liquid product as a function of temperature is shown in FIG. 1. The results showed that DMF conversion and para-xylene yield were both increased substantially with increasing reactor temperature, while the yield of byproduct HDO remained comparatively low at all temperatures. The commercial feasibility of a DMF to para-xylene step in an overall carbohydrate-based conversion process was therefore demonstrated.

EXAMPLE 4

Continuous Reaction Over a Fixed Bed of Catalyst

In a number of experiments demonstrating the continuous production of para-xylene, DMF at 2.5, 5, or 10 $cm^3$/hr and ethylene at 30, 50, or 100 $cm^3$/min were charged to a fixed bed of activated carbon catalyst. Two samples of different activated carbon types were evaluated for their catalytic activity for DMF conversion and selectivity to para-xylene. The reaction pressure was either 500 psig (35 barg) or 600 psig (41 barg) in the various experiments, designed to evaluate a number of specific reaction conditions. Reaction temperatures in the range from 200° C. (392° F.) to 335° C. (635° F.) were also studied.

The results showed that a per-pass conversion of DMF to para-xylene of 30% or more could be achieved at the conditions tested.

Without being bound by theory, it is believed from the results of the above examples that adsorption of the DMF and ethylene reactants by activated carbon or other porous materials described herein provides an important catalytic effect. The promotion of the desired conversion to para-xylene may, for example, be a result of interactions of the reactants DMF and ethylene on the surfaces of these materials or within their pores. These beneficial interactions may include enforcing a preferred reaction geometry, optimizing electronic interactions, and/or other effects that advantageously reduce activation energy and thereby catalyze the desired reaction pathway.

The invention claimed is:

1. A para-xylene production process comprising reacting 2,5-dimethylfuran (DMF) with ethylene under cycloaddition reaction conditions and in the presence of a catalyst selected from the group consisting of carbon and activated carbon to produce para-xylene.

2. The process of claim 1, wherein the cycloaddition reaction conditions include a temperature from about 100° C. (212° F.) to about 300° C. (572° F.).

3. The process of claim 1, wherein the cycloaddition reaction conditions include an ethylene partial pressure from about 10 barg (150 psig) to about 100 barg (1500 psig).

4. The process of claim 1, wherein the cycloaddition reaction conditions include a reactor residence time from about 1 hour to about 48 hours.

5. The process of claim 1, wherein the catalyst further comprises an alkali or alkaline earth metal promoter.

6. The process of claim 1, wherein the activated carbon is acid washed.

7. The process of claim 1, wherein the activated carbon has a surface area of at least about 700 $m^2$/gram and a total oxygen content of at least about 1% by weight.

8. The process of claim 1, comprising continuously feeding DMF and ethylene to, and continuously withdrawing the para-xylene from, a fixed bed of the catalyst.

9. The process of claim 1, wherein at least about 50% of the DMF is converted under the cycloaddition reaction conditions.

10. The process of claim 9, wherein the para-xylene is produced in an amount representing at least about 30% of a theoretical yield of para-xylene from the DMF.

11. The process of claim 1, wherein at least 6 of the carbon atoms of the para-xylene are derived from one or more annually renewable feedstocks.

12. The process of claim 11, wherein all carbon atoms of the para-xylene are derived from one or more annually renewable feedstocks.

13. The process of claim 1, wherein the DMF is obtained from conversion of a hexose.

14. The process of claim 13, wherein the hexose is glucose or fructose.

15. The process of claim 14, wherein the DMF is obtained from conversion of glucose or fructose to 5-hydroxymethylfurfural (HMF) followed by hydrogenation of the HMF to DMF.

16. A carbohydrate based process for producing para-xylene, comprising:
 (a) converting a hexose to 5-hydroxymethylfurfural (HMF);
 (b) hydrogenating the HMF to 2,5-dimethylfuran (DMF); and
 (c) reacting the 2,5-dimethylfuran (DMF) with ethylene under cycloaddition reaction conditions and in the presence of a catalyst selected from the group consisting of carbon and activated carbon to produce para-xylene.

17. The carbohydrate based process of claim 16, wherein the hexose is glucose or fructose.

18. A carbohydrate based process for producing terephthalic acid, comprising
 (a) converting a glucose or fructose to 5-hydroxymethylfurfural (HMF);
 (b) hydrogenating the HMF to 2,5-dimethylfuran (DMF);
 (c) reacting the DMF with ethylene under cycloaddition reaction conditions and in the presence of a catalyst selected from the group consisting of carbon and activated carbon to produce para-xylene; and
 (d) oxidizing the para-xylene with oxygen to produce terephthalic acid.

* * * * *